(12) United States Patent
Thomopoulos et al.

(10) Patent No.: US 9,375,516 B2
(45) Date of Patent: Jun. 28, 2016

(54) POLYMER NANOFIBER SCAFFOLD FOR A HEPARIN/FIBRIN BASED GROWTH FACTOR DELIVERY SYSTEM

(71) Applicant: Washington University in St. Louis, St. Louis, MO (US)

(72) Inventors: Stavros Thomopoulos, St. Louis, MO (US); Shelly Sakiyama-Elbert, St. Louis, MO (US); Matthew Silva, St. Louis, MO (US); Richard Gelberman, St. Louis, MO (US); Younan Xia, St. Louis, MO (US); Andrea Schwartz, St. Louis, MO (US); Jingwei Xie, Omaha, NE (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 87 days.

(21) Appl. No.: 14/158,011

(22) Filed: Jan. 17, 2014

(65) Prior Publication Data
US 2014/0135945 A1 May 15, 2014

Related U.S. Application Data

(62) Division of application No. 13/343,869, filed on Jan. 5, 2012, now Pat. No. 8,673,323.

(60) Provisional application No. 61/430,833, filed on Jan. 7, 2011.

(51) Int. Cl.
| | |
|---|---|
| A61L 27/54 | (2006.01) |
| A61L 27/26 | (2006.01) |
| A61L 27/18 | (2006.01) |
| C07K 14/475 | (2006.01) |
| C07K 14/75 | (2006.01) |
| C07K 14/47 | (2006.01) |
| C12N 9/74 | (2006.01) |
| A61K 38/00 | (2006.01) |
| A61F 2/30 | (2006.01) |

(52) U.S. Cl.
CPC ............... *A61L 27/54* (2013.01); *A61L 27/18* (2013.01); *A61L 27/26* (2013.01); *C07K 14/47* (2013.01); *C07K 14/475* (2013.01); *C07K 14/75* (2013.01); *C12N 9/6429* (2013.01); *A61F 2002/30766* (2013.01); *A61K 38/00* (2013.01); *Y10T 156/10* (2015.01)

(58) Field of Classification Search
CPC .............................. A61L 27/54; C07K 14/475
See application file for complete search history.

(56) References Cited

U.S. PATENT DOCUMENTS

| | | | |
|---|---|---|---|
| 6,468,731 B1 * | 10/2002 | Hubbell et al. ............... | 435/2 |
| 6,960,452 B2 | 11/2005 | Hubbell et al. | |
| 7,732,427 B2 | 6/2010 | Kiick et al. | |
| 2005/0031598 A1 | 2/2005 | Levenberg et al. | |
| 2005/0158357 A1 | 7/2005 | West et al. | |
| 2007/0269481 A1 | 11/2007 | Li et al. | |
| 2009/0192079 A1 | 7/2009 | Santos et al. | |
| 2010/0172952 A1 | 7/2010 | Srouji et al. | |
| 2010/0327494 A1 | 12/2010 | Jabbari | |

OTHER PUBLICATIONS

Chew et al. (The role of electrospinning in the emerging field of nanomedicine, Curr Pharm Des. 2006; 12: 4751).*
Li et al. (Fabrication and characterization of six electrospun poly(alpha-hydroxy ester)-based fibrous scaffold for tissue engineering applications, Acta Biomater. 2006; 2:377).*
Moutos et al. (Tissue Engineering: Part A. 2010; 16(4): 1291-1301).*
Chung et al. (Advanced Drug Delivery Reviews. 2007; 59:249-262).*
Gelberman et al., "The early effects of sustained platelet derived growth factor administration on the functional and structural properties of repaired intrasynovial flexor tendons: An in vivo biomechanical study at the three week interval in canines", Journal of Hand Surgery (American), 2007, pp. 373-379, vol. 32, No. 3.
Li et al., "Nanofiber scaffolds with gradations in mineral content for mimicking the tendon-to-bone insertion site", Nano Letters, 2009, pp. 2763-6768, vol. 9, No. 7.
Sakiyama-Elbert et al., "Development of fibrin derivatives for controlled release of heparin-binding growth factors", Journal of Control Release, 2000, pp. 289-402, vol. 65, No. 3.
Sakiyama-Elbert et al., "Controlled release kinetics and biologic activity of PDGF-BB for use in flexor tendon repair", Journal of Hand Surgery (American), 2008, pp. 1548-1557, vol. 33, No. 9.
Thomopoulos et al., "PDGF-BB released in tendon repair using a novel delivery system promotes cell proliferation and collagen remodeling", Journal of Orthopaedic Research, 2007, pp. 1358-1368, vol. 25, No. 10.
Thomopoulos et al., "Enhanced flexon tendon healing through sustained delivery of PDGF-BB", Journal of Orthopaedic Research, 2009, pp. 1209-1215, vol. 27, No. 9.
Thomopoulos et al., "Controlled release and biologic activity by tendon fibroblasts in vitro", Annals of Biomedical Engineering, 2010, pp. 225-234, vol. 38, No. 2.
Chung et al., "Surface engineered and drug releasing pre-fabricated scaffolds for tissue engineering," Advanced Drug Delivery Reviews, 2007, pp. 249-262, vol. 59.
Willerth et al., "Approaches to neural tissue engineering using scaffolds for drug delivery," Advanced Drug Delivery Reviews, 2007, pp. 325-338, vol. 59.
Jiang et al., "Pluripotency of mesenchymal stem cells derived from adult marrow," Nature, 2002, pp. 41-49, vol. 418.

* cited by examiner

*Primary Examiner* — Scott Long
(74) *Attorney, Agent, or Firm* — Polsinelli PC

(57) ABSTRACT

A growth factor delivery scaffold combines a heparin/fibrin-based delivery system (HBDS) with a backbone based on polymer nanofibers for tissue (e.g., tendon and ligament) repair. The scaffold has improved surgical handling properties compared to the gelatinous consistency of the prior art HBDS system and retains the capability for delivering mesenchymal cells and controlling the release of growth factors. One application for the scaffold is mesenchymal stem cell (MSC) therapy for flexor tendon repair. The scaffold can deliver growth factors in a sustained manner, can be implanted for flexor tendon repair, is biocompatible, and is not cytotoxic. The growth factor delivery scaffold may also be used in the surgical repair of an injury to bone, muscle, cartilage, or other tissues.

12 Claims, 13 Drawing Sheets

POLYMER NANOFIBER SCAFFOLD FOR A HEPARIN/FIBRIN BASED GROWTH FACTOR DELIVERY SYSTEM

CROSS-REFERENCE TO RELATED APPLICATIONS

This application is a divisional application of U.S. patent application Ser. No. 13/343,869, filed Jan. 5, 2012, which claims the benefit of U.S. Provisional Application No. 61/430,833 filed Jan. 7, 2011, both of which are incorporated herein by reference in their entirety.

FEDERALLY SPONSORED RESEARCH

This invention was made with government support under grant numbers DP1 OD000798-04 and R01 AR033097 awarded by the National Institute of Health. The government has certain rights in the invention.

REFERENCE TO A SEQUENCE LISTING

This application includes a Sequence Listing. A paper copy of the Sequence Listing and a computer readable form of the Sequence Listing containing the file named 15060-442_ST25.txt, which is 950 bytes in size (as measured in MICROSOFT WINDOWS® EXPLORER), are provided herein and are herein incorporated by reference. This Sequence Listing consists of SEQ ID NO:1.

BACKGROUND

Embodiments described herein relate generally to polymer nanofiber scaffold for a heparin/fibrin based growth factor delivery system and, more particularly, to a polylactic glycolic acid nanofiber mat layered with a fibrinogen solution including heparin, fibrinogen, heparin-binding peptide, growth factor, and mesenchymal stem cells for use in tissue repair.

Growth factors drive biology and the differentiation of mesenchymal stem cells. Mesenchymal stem cells combined with a sustained supply of appropriate growth factors at the site of a structural tissue injury aid in repairing the injury.

A first prior art growth factor delivery system is fibrin gel encapsulating a mixture of heparin, growth factor, and mesenchymal stem cells. A second prior art growth factor delivery system is disclosed in U.S. Pat. No. 6,468,731 issued Oct. 22, 2002 and U.S. Pat. No. 6,960,452 issued Nov. 1, 2005, the entire disclosures of which are incorporated herein by reference. In this second prior art growth factor delivery system, a heparin-binding peptide or protein is added to the fibrin gel, and the heparin-binding peptide binds to the fibrin molecules and heparin molecules. The growth factor is bound to the heparin, and mesenchymal stem cells are mixed into the fibrin gel. The addition of the heparin-binding peptide extends the release of the growth factor. Fibrin gel alone is difficult to handle, surgically implant, and retain at an injury site due to its gelatinous consistency.

BRIEF DESCRIPTION OF THE DRAWINGS

The embodiments described herein may be better understood by referring to the following description in conjunction with the accompanying drawings.

DETAILED DESCRIPTION

In some embodiments, a growth factor delivery scaffold combines a heparin/fibrin-based delivery system (HBDS) with a backbone based on polymer nanofibers for tissue (e.g., tendon and ligament) repair. The scaffold has improved surgical handling properties compared to the gelatinous consistency of the prior art HBDS system and retains the capability for delivering mesenchymal cells and controlling the release of growth factors. One application for the scaffold is mesenchymal stem cell (MSC) therapy for flexor tendon repair. The scaffold can deliver growth factors in a sustained manner, can be implanted for flexor tendon repair, is biocompatible, and is not cytotoxic. The growth factor delivery scaffold may also be used in the surgical repair of an injury to bone, muscle, cartilage, or other tissues.

In some embodiments, the scaffold consists of six alternating layers of electrospun poly lactic glycolic acid (PLGA) nanofiber mats and HBDS. PLGA polymer nanofiber mats are biodegradable in water and have attractive mechanical properties. For PLGA 85:15, the decrease in mechanical integrity occurs after 1-2 months in an aqueous environment, and the loss of mass occurs after approximately 3-4 months. PLGA 85:15 is prepared by dissolving PLGA (85:15, MW 50,000-75,000) in dichloromethane (DCM) and electrospinning the 200 mg/mL solution.

Figure 1:
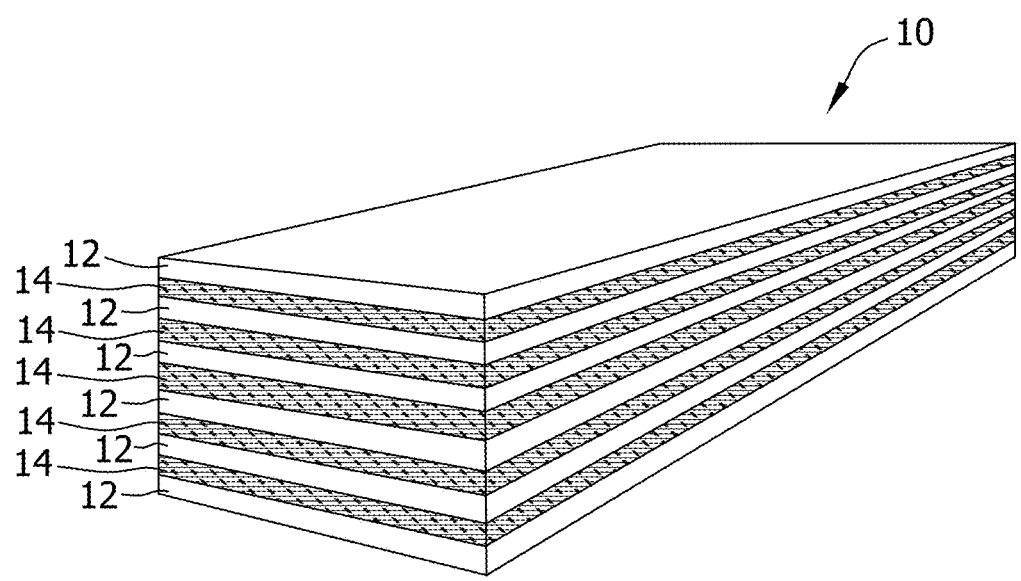
FIG. 1 is a schematic diagram of a scaffold according to an embodiment of the disclosure.
Figure 2:
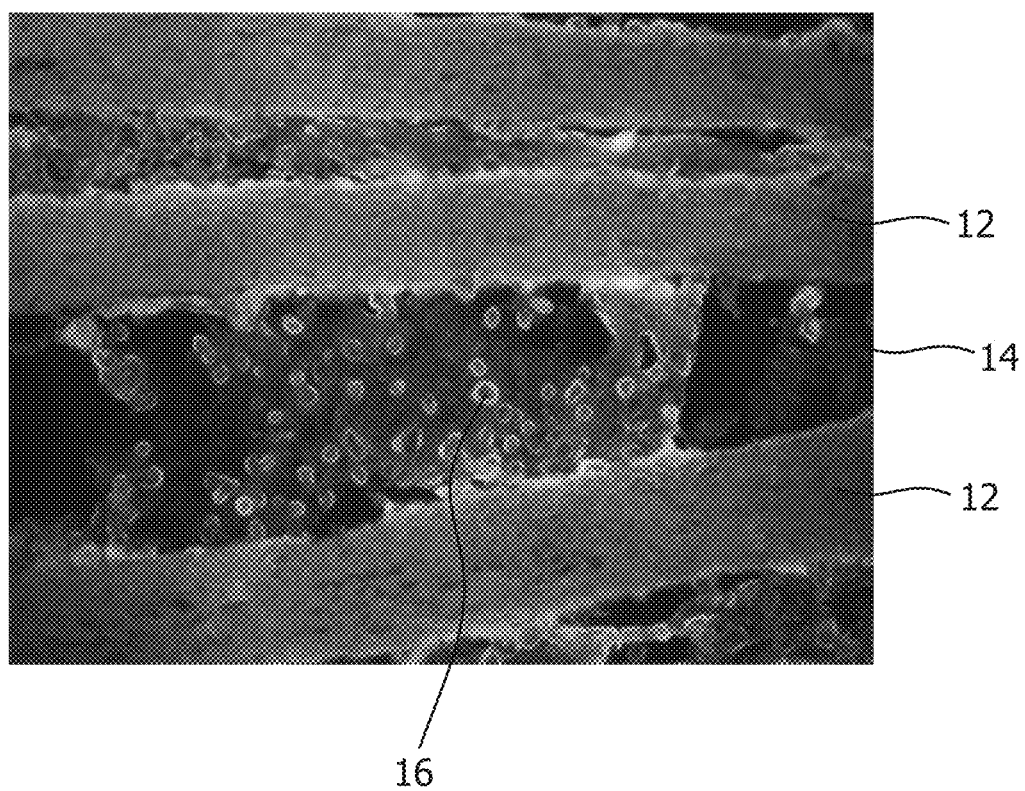
FIG. 2 is a micrograph image of a region of a scaffold according to an embodiment of the disclosure.

FIG. 1 is a schematic diagram of an exemplary scaffold 10. FIG. 2 is a micrograph image of a region of an exemplary scaffold, such as scaffold 10 (shown in FIG. 1). Scaffold 10 includes six alternating layers of PLGA nanofiber mats 12 and HBDS 14. In the exemplary embodiment, HBDS 14 includes $1 \times 10^6$ adipose derived (AD) MSCs 16.

Figure 3:
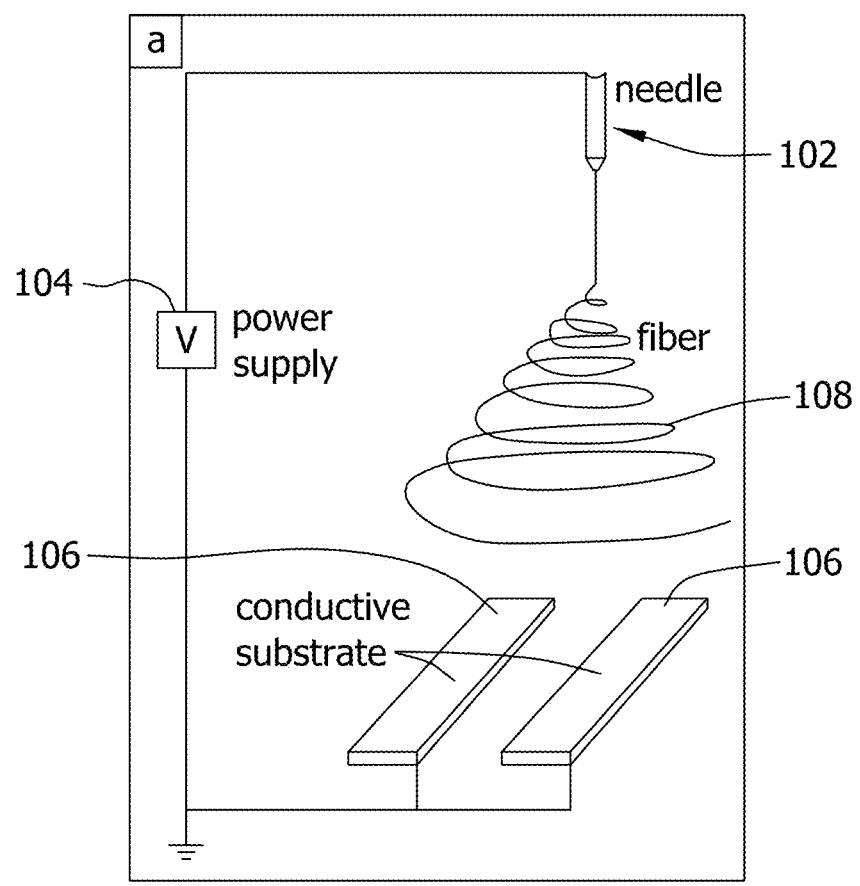
FIG. 3 is a schematic diagram of an electrospinning apparatus for producing a polymer nanofiber mat according to an embodiment of the disclosure.

Referring to FIG. 3, the PLGA solution is loaded into a plastic syringe equipped with a 23 gauge stainless steel needle 102. The needle 102 is connected to a high-voltage supply 104 such as the ES30P-5W available from Gamma High Voltage Research of Ormond Beach, Fla. (maximum voltage=30 kV). The feed rate for the PLGA solution is controlled using a syringe pump such as the KDS-200 available from Stoelting of Wood Dale, Ill. The concentration of PLGA in the PLGA solution and the flow rate are controlled to generate nanofibers with diameters of 100-500 nm. This same procedure can also be used to generate PLGA nanofibers with compositions other than 85:15.

Polymer nanofiber mats containing well-aligned nanofibers are fabricated to guide the regeneration of well-organized tissue (e.g., tendon tissue). To fabricate aligned nanofiber mats, two pieces of conductive substrates 106 separated by a void gap of 1-2 cm in width are located 5 cm below the needle 102 tip. In one embodiment, the substrates 106 are 5 cm long, although there is no limitation for their length. The substrates 106 are grounded, so the voltage differential between them is zero. During electrospinning, nanofibers 108 are formed from the PLGA solution and stretched and aligned into a uniaxial array across the gap with their longitudinal axes oriented perpendicular to the longitudinal axes of the conductive substrates 106. The fibers 108 are released from the collectors and used as free-standing polymer nanofiber mats.

Figure 4:
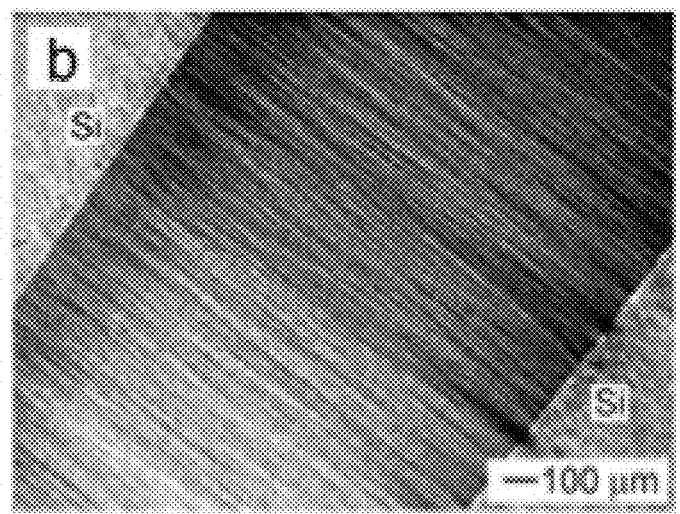
FIG. 4 is a dark field optical micrograph of an aligned array of nanofibers (i.e., a polymer nanofiber mat) according to an embodiment of the disclosure.
Figure 5:
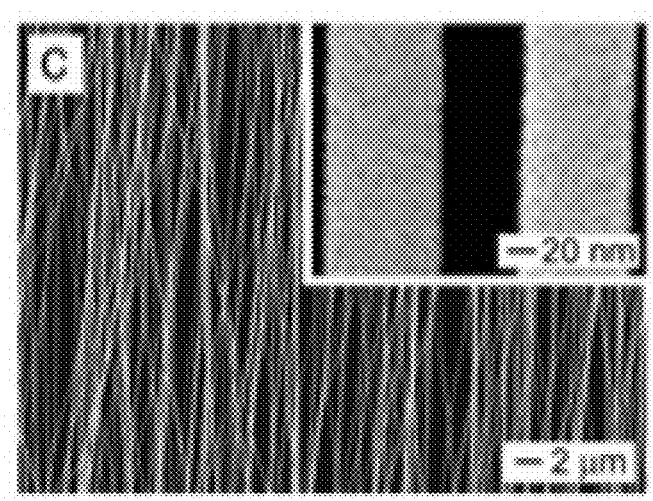
FIG. 5 is a scanning electron microscopy image of an aligned array of nanofibers according to an embodiment of the disclosure.

Referring to FIG. 4, a dark-field optical micrograph of an aligned array of nanofibers that were fabricated as described above is shown on a 100 micron scale. The nanofibers 108 are aligned longitudinally between the conductors 106. FIG. 5 shows the aligned nanofibers 108 on a 2 micron scale with an inset of two individual nanofibers 108 on a 20 nanometer scale.

The HBDS (i.e., fibrin gel) includes a bidomain peptide (i.e., a heparin-binding peptide or protein) with a factor XIIIa substrate derived from α2-plasmin inhibitor at the N terminus and a C-terminal heparin-binding domain. The bidomain peptide is covalently cross-linked to a fibrin matrix during coagulation by the transglutaminase activity of factor XIIIa. The heparin-binding peptide immobilizes heparin electrostatically to the fibrin matrix which in turn immobilizes the heparin-binding growth factor, slowing its diffusion from the matrix.

In some embodiments, a fibrinogen solution which is later cured into the fibrin gel is made with the following final component concentrations: 7.5 mg/mL of human fibrinogen concentration such as that available from EMD Bio of San Diego, Calif.; 6.9 mmol/L of $CaCl_2$; 12.5 units/mL of thrombin; 0.53 mmol/L of peptide with sequence dLNQEQVSPK (βA)FAKLAARLYRKA-NH2 (SEQ ID NO:1) where dL denotes dansyl leucine; and 110 μmol/mL of heparin (Sigma, H-9399) in tris-buffered saline (TBS) (137 mmol/L of NaCl, 2.7 mmol/L of KCl, and 33 mmol/L tris at a pH of 7.4). The fibrinogen solution is polymerized directly on the polymer nanofiber (PLGA) mat, effectively serving as a bond between layers. It is believed that the fibrinogen solution fills pores in the polymer nanofiber mat prior to polymerization and mechanically links the layer of resultant fibrin gel to the adjacent polymer nanofiber mats. For cellular scaffolds, mesenchymal stem cells are incorporated into the fibrinogen solution prior to polymerization (i.e, curing).

In some embodiments, the HBDS delivers tendon specific growth factors BMP-12 (779-G7-010, R & D Systems) and BMP-14 (853-G5-050, R & D Systems) in a sustained manner and serves as the delivery vehicle for the mesenchymal stem cells. In some embodiments, the HBDS delivers PDGF. The PLGA nanofiber mat adds mechanical integrity to the scaffold, allowing a surgeon to manipulate and implant the scaffold and maintain the growth factors and mesenchymal stem cells at the site of an injured tissue. In some embodiments, a growth factor delivery system for flexor tendon repair comprises 6 alternating layers of HBDS (i.e., fibrin gel) and polymer nanofiber mats. This volume of scaffold allows for delivery of more than 1 million cells to the repair site without adding bulk to the tendon at the site of a structural injury.

Figure 6:
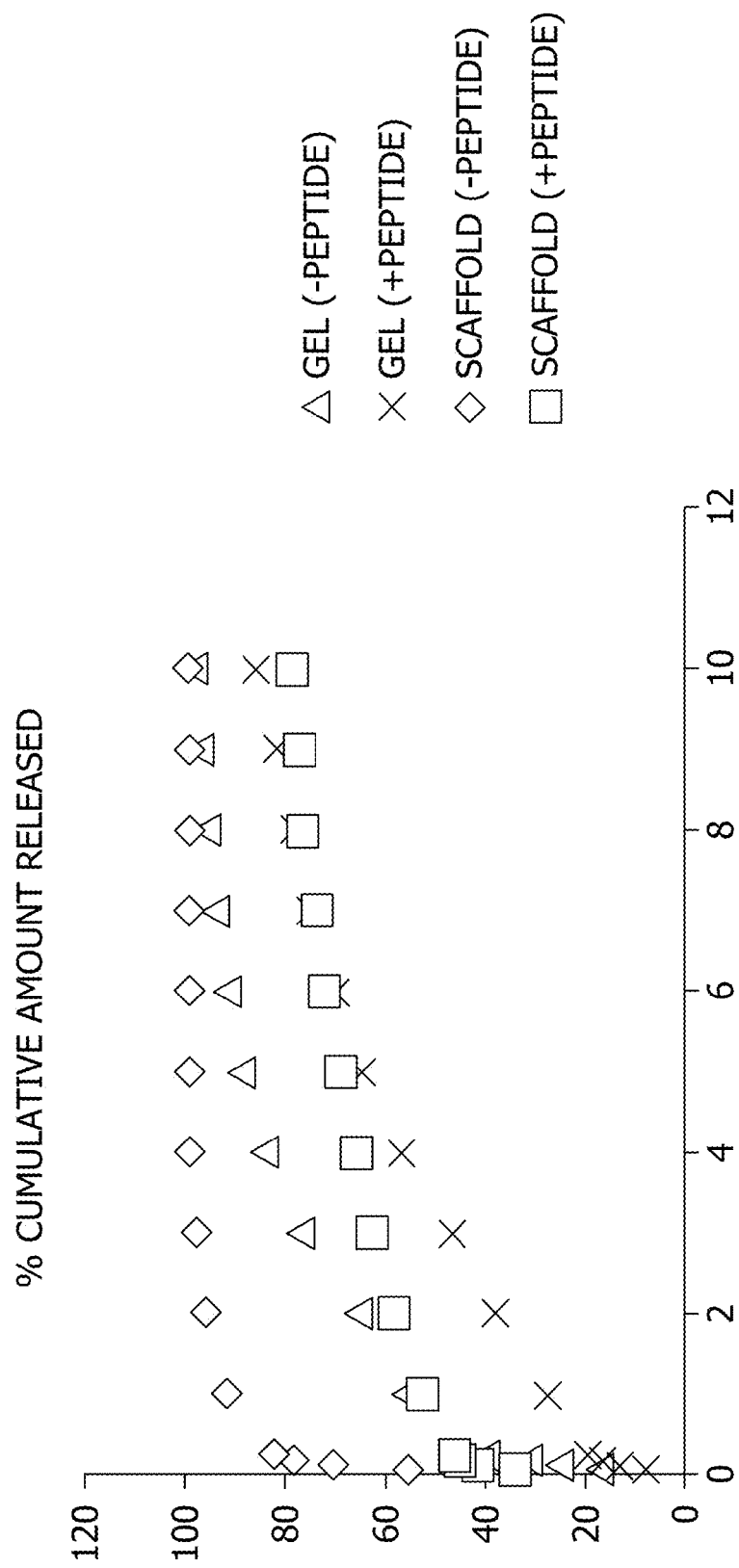
FIG. 6 is a plot of cumulative percentage of growth factor released versus number of days for a variety of growth factor delivery systems according to an embodiment of the disclosure.

Referring to FIG. 6, a plot of cumulative growth factor released versus days in vivo shows that the growth factor delivery scaffold does not substantially alter the release rate of growth factor of a given growth factor delivery system. The growth factor delivered in the plot of FIG. 6 is PDGF-BB. FIG. 6 compares a fibrin gel without a heparin-binding peptide, a fibrin gel with a heparin-binding peptide, a scaffold including a fibrin gel without a heparin-binding peptide, and a scaffold including a fibrin gel with a heparin-binding peptide. The scaffold (i.e., alternating layers of polymer nanofiber mat and fibrin gel) retains the sustained release of growth factor while improving the handling characteristics of the fibrin gel and the retention of the growth factor and mesenchymal stem cells at the site of a tissue injury (i.e., in a break, tear, rupture, or cut).

Figure 7:
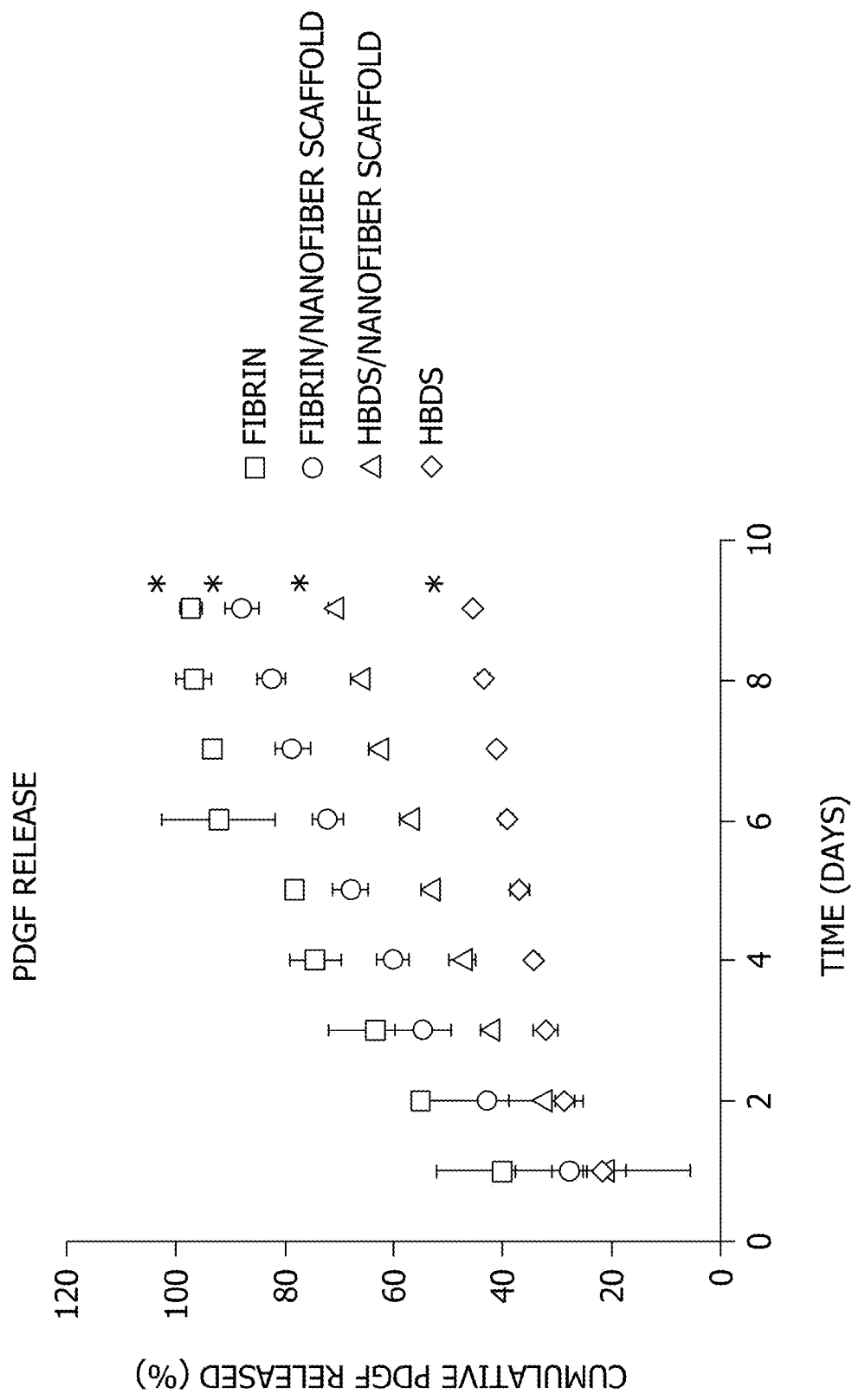
FIG. 7 is a plot of cumulative percentage of growth factor released versus number of days for a variety of growth factor delivery systems according to an embodiment of the disclosure.

FIG. 7 is a plot of cumulative percentage of growth factor released versus number of days for a variety of growth factor delivery systems according to an embodiment of the disclosure. The growth factor delivered in the plot of FIG. 7 is PDGF-BB. FIG. 7 compares a fibrin gel alone, a fibrin gel/nanofiber scaffold, a HBDS/nanofiber scaffold, and an HBDS alone.

In some embodiments, mesenchymal stem cells may be isolated from bone marrow by extraction from the left and right proximal humeri using a drill such as an EZ-IO drill available from Vidacare of Shivano Park, Tex. The cells are spun down, re-suspended in 10 mL of complete α-MEM, and plated in a 60 mm Petri dish in an incubator at 37° C. with 5% $CO_2$. After 24 hours, the medium is removed (thus removing non-adherent hematopoietic cells) and replaced with 5 mL of fresh medium. The cells are then grown under standard culture conditions in an incubator at 37° C. with 5% $CO_2$. To track in vivo use, 1 million autologous cells are labeled with the fluorescent cell membrane dye DiI available from Invitrogen of Carlsbad, Calif. and seeded into a growth factor delivery scaffold having dimensions: 7 mm long, 2.5 mm wide, and 1.5 mm thick.

One embodiment of the disclosure was evaluated via intra-synovial flexor tendon repair in a clinically relevant animal model (i.e., adult mongrel dogs). Adult mongrel dogs have flexor tendon anatomic similarities to humans and are large enough to perform a surgical repair that is identical to the repair used in human clinical practice. Post-operative rehabilitation was controlled using a removable cast system which replicated the controlled motion therapy that human patients receive after tendon repair. Dogs weighing 20 to 30 kilograms were obtained from Covance Research and primary midsubstance tendon repair was performed under sterile conditions in an animal operating facility. The flexor tendons of the left second and fifth toes were approached through separate midlateral incisions. For flexor tendon injury and repair, the flexor digitorum profundus tendon was transected sharply at the level of the proximal interphalangeal joint between the A-2 and A-4 pulleys. Operative repair was carried out with an 8-strand suture of 4-0 multifilament nylon such as 4-0 Supramid available from S. Jackson of Alexandria, Va. Longitudinally oriented horizontal slits were created in the center of each tendon stump using a beaver blade (5 mm depth, 2.5 mm width). The HBDS/nanofiber scaffold was secured within the injury site by a core suture and sealed in that location by a 6-0 nylon running epitenon suture.

Figure 10:
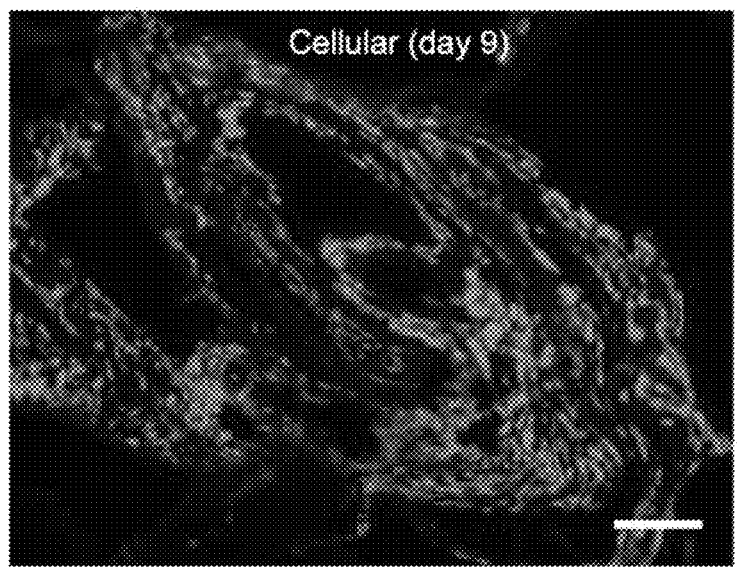
FIG. 10 is an image of a section of growth factor delivery scaffold at 9 days after implantation including the mesenchymal stem cells labeled with the fluorescent membrane dye.

Based on histologic analysis, the scaffold remains at the repair site and the autologous mesenchymal stem cells are viable for at least 9 days post-implantation as shown in FIG. 10. This animal model, which is identical to that used in prior tendon repair trials, utilizes the flexor tendons of two toes of each forepaw. There was no cross contamination of biological and biomechanical information, and the findings in each toe are not interactive with each other. Utilizing two tendons per paw maximizes the information obtained from each experimental animal and makes pair-wise comparisons between groups possible. Postoperatively, the treated forelimbs were immobilized using fiberglass shoulder spica casts with the elbows at 90 degrees and the wrists at 70 degrees flexion. The fore-paw portion of the casts were bi-valved to allow for controlled passive mobilization during two 5-minute rehabilitation sessions performed 5 days a week starting on the first post-operative day. The in vivo tendon loading produced by the mobilization protocol is well-characterized.

Figure 8:
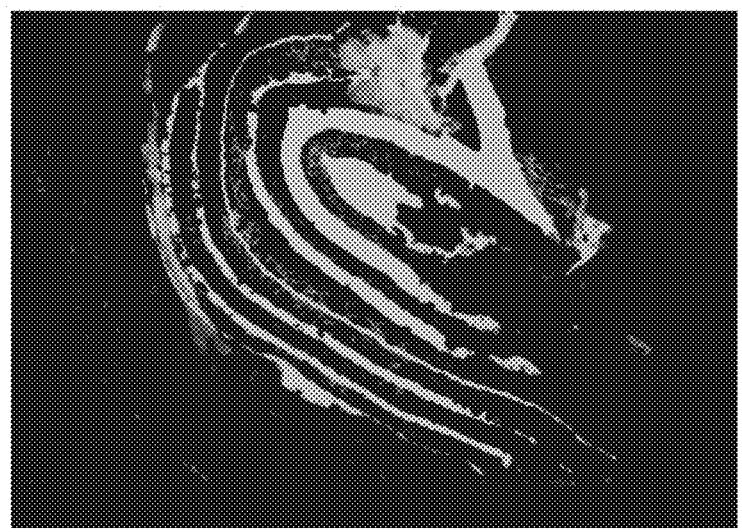
FIG. 8 is an image of a section of growth factor delivery scaffold after 9 days of implantation in a canine flexor tendon injury wherein the nanofiber mat has been labeled with fluorescein isothiocyanate (FITC) according to an embodiment of the disclosure.
Figure 9:
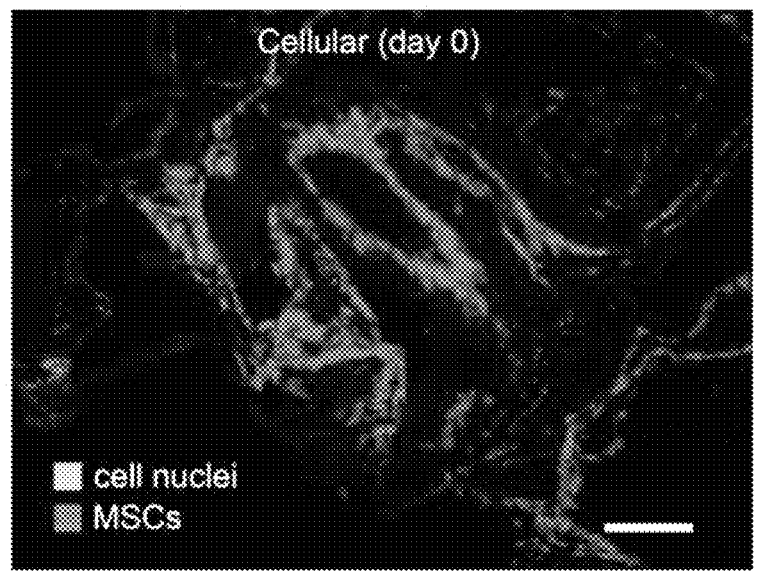
FIG. 9 is an image of a section of growth factor delivery scaffold at the time of implantation including mesenchymal stem cells labeled with a fluorescent membrane dye at according to an embodiment of the disclosure.
Figure 11:
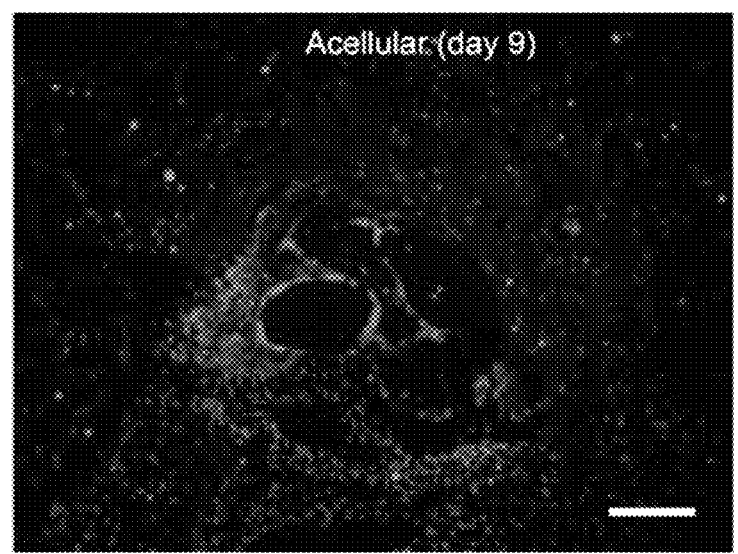
FIG. 11 is an image of a section of growth factor delivery scaffold at 9 days after implantation that does not include the mesenchymal stem cells showing the cell nuclei of the native tendon cells.

FIG. 8 shows the HBDS/nanofiber growth factor delivery scaffold 9 days after implantation. The PLGA nanofiber mat is labeled with fluorescein isothiocyanate (FITC) and exposed to UV light, and six alternating layers of HBDS (i.e., fibrin gel) and PLGA (i.e., polymer nanofiber mat) can be seen. FIGS. 9-11 show frozen sections of the growth factor delivery scaffold including mesenchymal stem cells via a 10× objective relative to a 200 micron scale bar. The mesenchymal stem cells are labeled with a fluorescent membrane dye (i.e., DiI) prior to implantation. FIG. 9 shows the section at the time of implantation (i.e., tissue repair or time zero) and FIGS. 10 and 11 show the section at 9 days after implantation. FIG. 10 shows a scaffold with fluorescently labeled mesenchymal stem cells while FIG. 11 shows a scaffold without mesenchymal stem cells (the cell nuclei of the native tendon cells are visible).

Figure 12:
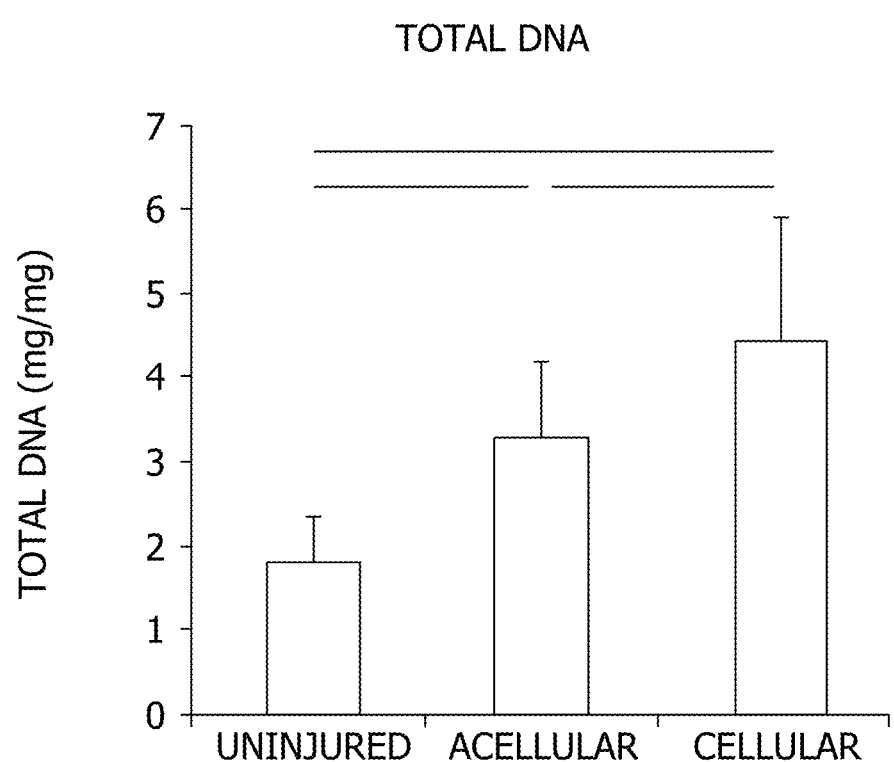
FIG. 12 is a plot of total DNA content for a variety of tendons.

FIG. 12 is a plot of total DNA content for a variety of tendons. The plot shows total DNA in units of mg/mg for uninjured tendons, repaired tendons that received a cellular scaffold including AD-MSCs, and repaired tendons that received an acellular scaffold including cytotoxic T lymphocytes (CTL). The plot indicates significant differences in the total DNA content between the different tendons.

Figure 13:
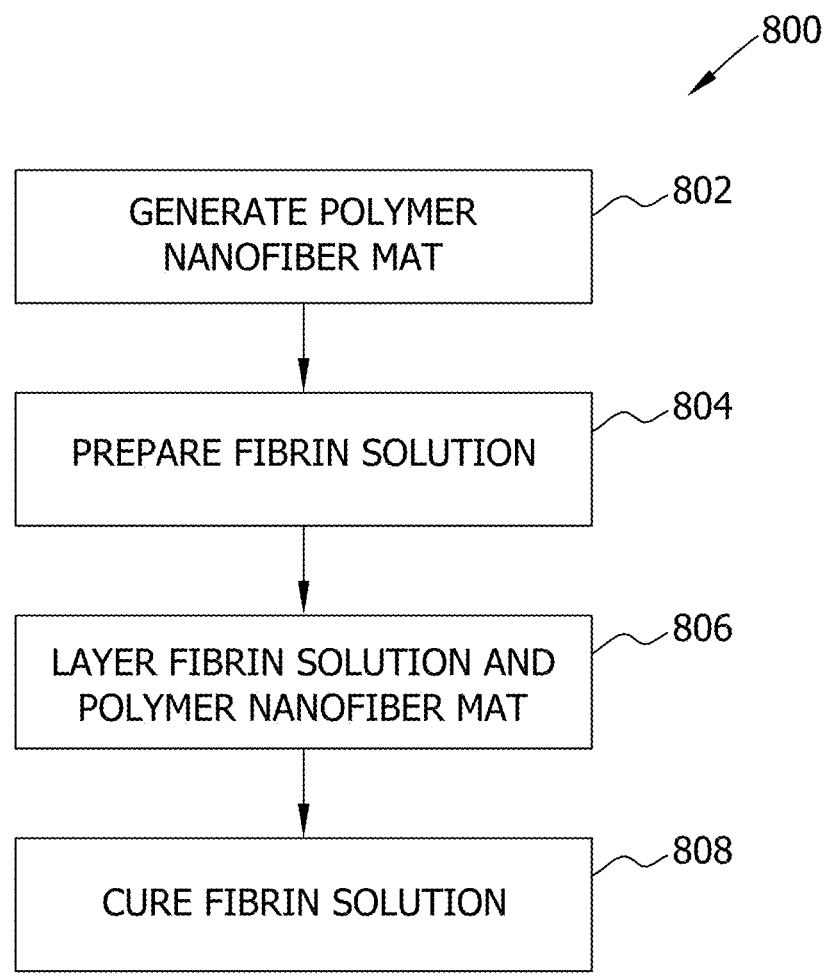
FIG. 13 is a flow chart showing a method of producing a growth factor delivery scaffold according to an embodiment of the disclosure.

Referring to FIG. 13, a method 800 of producing a growth factor delivery scaffold is shown according to an embodiment of the disclosure. At 802, a polymer nanofiber mat is generated by electrospinning polylactic co-glycolic acid (PLGA) dissolved in dichoromethane over parallel conductors. At 804, a fibrinogen solution is prepared by mixing mesenchymal stem cells, fibrinogen, heparin, a heparin-binding peptide, a growth factor, and thrombin together. At 806, pieces of the generated polymer nanofiber mat are layered with the fibrinogen solution. At 808, the fibrinogen solution is cured into a fibrin gel to produce the growth factor delivery system scaffold. Curing at 808 includes allowing time for the thrombin to convert the fibrinogen into fibrin and may optionally include controlling the temperature and/or humidity of the scaffold during curing.

Figure 14:
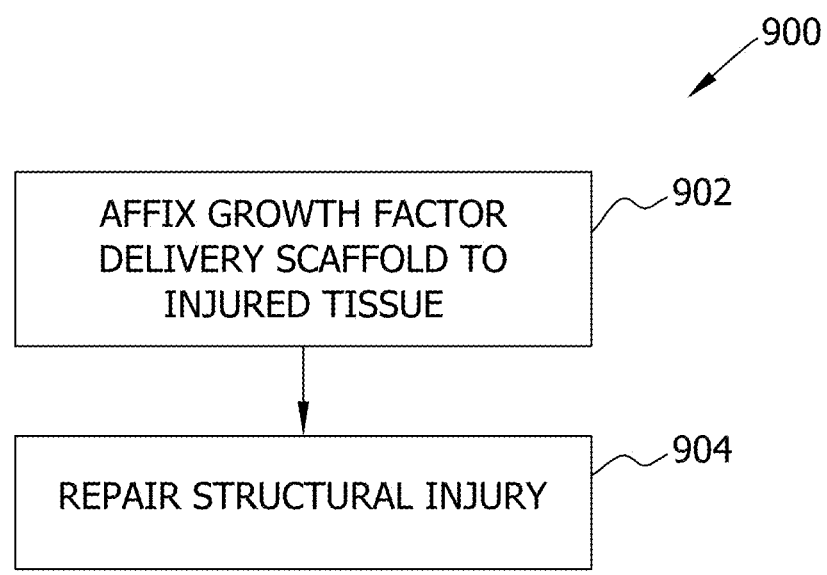
FIG. 14 is a flow chart showing a method of repairing an injured tissue according to an embodiment of the disclosure.

Referring to FIG. 14, a method 900 of repairing an injured tissue using the growth factor delivery scaffold produced via the method 800 of FIG. 13 begins at 902 with affixing the produced growth factor delivery scaffold to the injured tissue. This may be accomplished by, for example, a suture. The growth factor delivery scaffold is affixed within a space created by the structural injury and does not bear the load of the injured tissue. At 904, the structural injury is repaired such that the growth factor delivery scaffold is retained at the site of the injury. This may be accomplished by, for example, suturing a rupture, cut, or break such that the growth factor delivery scaffold is enclosed.

Figure 15:
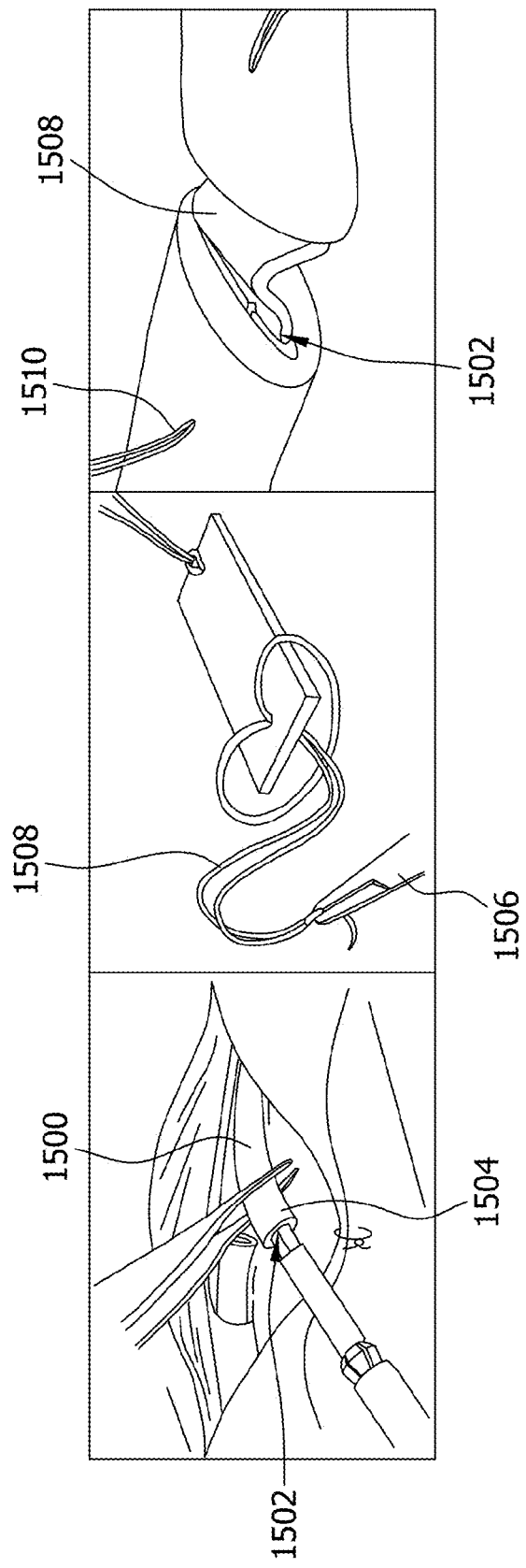
FIGS. 15A-15C illustrate a surgical method of repairing an injured tissue according to an embodiment of the disclosure.

FIGS. 15A-15C illustrate a surgical method of repairing an injured tissue according to an embodiment of the disclosure. As shown in FIG. 15A, a flexor tendon 1500 is transected, and longitudinally oriented horizontal slits 1502 are created in each tendon stump 1504. As shown in FIG. 15B, sutures 1506 are used to grab an HBDS/nanofiber scaffold 1508. As shown in FIG. 15C, HBDS/nanofiber scaffold 1508 is secured within the slits 1502, and a running epitenon suture 1510 is used to seal HBDS/nanofiber scaffold 1508 in that location.

Figure 16:
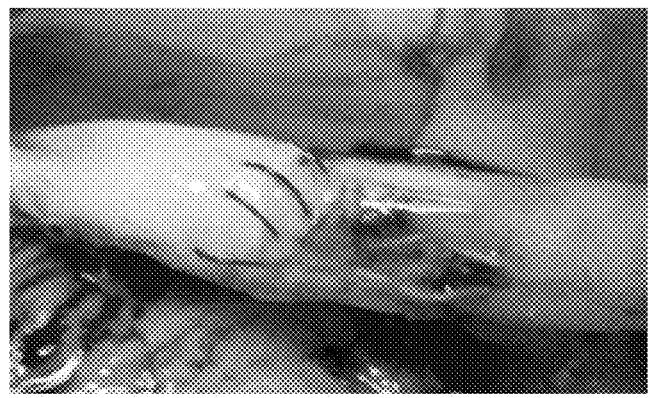
FIG. 16 is an image of a tendon repaired using the surgical method shown in FIGS. 15A-15C.

FIG. 16 is an image of a tendon repaired using the surgical method shown in FIGS. 15A-15C taken nine days post-operatively. Notably, as shown in FIG. 16, no gapping is visible at the repair site, and no adhesions are visible between the tendon and the sheath.

The order of execution or performance of the operations in the embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or embodiments thereof, the articles "a," "an," "the," and "said" are intended to mean that there are one or more of the elements. The terms "comprising," including," and "having" are intended to be inclusive and mean that there may be additional elements other than the listed elements.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A growth factor delivery scaffold comprising:
a plurality of uniaxial polymer nanofiber mats; and
a cured fibrin gel on the polymer nanofiber mats;
wherein the cured fibrin gel comprises fibrin, heparin, a heparin-binding peptide, a growth factor, and thrombin; and
wherein the scaffold comprises alternating layers of the polymer nanofiber mats and the cured fibrin gel.

2. The growth factor delivery scaffold of claim 1, wherein the polymer nanofiber mats comprise electrospun polylactic co-glycolic acid.

3. The growth factor delivery scaffold of claim 1, wherein the cured fibrin gel further comprises mesenchymal stem cells.

4. The growth factor delivery scaffold of claim 1 wherein a first end of the heparin-binding peptide is cross-linked to the fibrin, a second end of the heparin-binding peptide is electrostatically bonded to the heparin, and the growth factor is bonded to the heparin.

5. The growth factor delivery scaffold of claim 1, wherein the scaffold comprises six alternating layers of the polymer nanofiber mats and the cured fibrin gel.

6. The growth factor delivery scaffold of claim 1, wherein the polymer nanofiber mats comprise nanofibers having diameters of from 100 nm to 500 nm.

7. A method of repairing an injured tissue comprising:
affixing the growth factor delivery scaffold of claim 1 to the injured tissue, wherein:
the injury to the tissue is a structural injury; and
the growth factor delivery scaffold is affixed within the structural injury; and
repairing the structural injury of the injured tissue such that the growth factor delivery scaffold is retained at the site of the structural injury.

8. The method of claim 7 wherein the growth factor delivery scaffold is affixed to the injured tissue in a space created by the structural injury, and the structural injury is repaired such that the growth factor delivery scaffold does not bear a load of the injured tissue and the growth factor delivery scaffold is retained within a space created by the structural injury.

9. The method of claim 8 wherein repairing the structural injury comprises suturing edges of the injured tissue together around the space created by the structural injury.

10. The method of claim 7 wherein the structural injury is a rupture, tear or break.

11. The method of claim 7 wherein affixing the growth factor delivery scaffold comprises suturing the growth factor delivery scaffold to the injured tissue.

12. The method of claim 7 wherein the injured tissue comprises at least one of tendon, cartilage, bladder, muscle, or bone.

* * * * *

SEQUENCE LISTING

```
<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Dansyl Leucine

<400> SEQUENCE: 1

Leu Asn Gln Glu Gln Val Ser Pro Lys Ala Phe Ala Lys Leu Ala Ala
1               5                   10                  15

Arg Leu Tyr Arg Lys Ala
            20
```